US012240805B2

United States Patent
Ren et al.

(10) Patent No.: US 12,240,805 B2
(45) Date of Patent: Mar. 4, 2025

(54) METHOD FOR PRODUCING 1,4-DIMETHYLNAPHTHALENE

(71) Applicants: Sinochem Hebei Fuheng Co., LTD, Hebei (CN); Sato Planning Co., Ltd, Ibaraki (JP)

(72) Inventors: Jianpo Ren, Hebei (CN); Lieyi Ji, Hebei (CN); Junsheng Wang, Hebei (CN); Zhiqiang Jiang, Hebei (CN)

(73) Assignees: Sinochem Hebei Fuheng Co., Ltd, Hebei (CN); Sato Planning Co., Ltd, Ibaraki (JP)

( * ) Notice: Subject to any disclaimer, the term of this patent is extended or adjusted under 35 U.S.C. 154(b) by 0 days.

(21) Appl. No.: 17/928,700

(22) PCT Filed: Aug. 10, 2021

(86) PCT No.: PCT/CN2021/111655
§ 371 (c)(1),
(2) Date: Nov. 30, 2022

(87) PCT Pub. No.: WO2022/257260
PCT Pub. Date: Dec. 15, 2022

(65) Prior Publication Data
US 2024/0228406 A1 Jul. 11, 2024

(30) Foreign Application Priority Data

Jun. 7, 2021 (CN) .......................... 202110633219.5

(51) Int. Cl.
*C07C 5/41* (2006.01)
*B01J 21/12* (2006.01)

(52) U.S. Cl.
CPC ................. *C07C 5/41* (2013.01); *B01J 21/12* (2013.01); *C07C 2521/12* (2013.01); *C07C 2531/025* (2013.01)

(58) Field of Classification Search
None
See application file for complete search history.

(56) References Cited

U.S. PATENT DOCUMENTS

| | | | |
|---|---|---|---|
| 3,775,497 A | 11/1973 | Thompson |
| 3,781,375 A | 12/1973 | Shima et al. |
| 4,950,825 A | 8/1990 | Sikkenga et al. |
| 5,034,561 A | 7/1991 | Sikkenga et al. |
| 5,284,987 A | 2/1994 | Sikkenga et al. |
| 5,396,007 A | 3/1995 | Kyuko et al. |
| 5,401,892 A | 3/1995 | Sikkenga et al. |
| 6,504,069 B1 | 1/2003 | Kyuuko et al. |
| 2007/0232842 A1 | 10/2007 | Soh et al. |
| 2008/0051618 A1 | 2/2008 | Kim et al. |

FOREIGN PATENT DOCUMENTS

| | | |
|---|---|---|
| CN | 1038805 A | 1/1990 |
| CN | 101050161 A | 10/2007 |
| CN | 101130468 A | 2/2008 |
| GB | 1430025 A | 3/1976 |
| JP | 4867261 A | 9/1973 |
| JP | 4875557 A | 10/1973 |
| JP | 4948647 A | 5/1974 |
| JP | 4993348 A | 9/1974 |
| JP | 5031150 B1 | 10/1975 |
| JP | 6027694 A | 2/1985 |
| JP | 62240632 A | 10/1987 |
| JP | 03500052 A | 1/1991 |
| JP | 05213782 A | 8/1993 |
| JP | 0672910 A | 3/1994 |
| JP | 0761941 A | 3/1995 |
| JP | 0769942 A | 3/1995 |
| JP | 2000239194 A | 9/2000 |
| JP | 200670000 A | 3/2006 |
| JP | 2006199689 A | 8/2006 |
| KR | 20070099241 A | 10/2007 |

OTHER PUBLICATIONS

Machine translation JP 2006-070000. Retrieved May 13, 2024 (Year: 2024).*
International Search Report and Written Opinion for International Application No. PCT/CN2021/111655, dated Dec. 22, 2021, 10 pages. (Partial English translation).
Extended European Search Report for European Application No. 21943312.5, dated Dec. 11, 2023, 8 pages.
Japanese Notice of Reasons for Refusal for Japanese Application No. 2022-574268, mailed Jan. 9, 2024 with translation, 6 pages.
Molnár et al., "Alkylation of Benzene with Cyclic Ethers in Superacidic Media", Catalysis Letters, (Apr. 11, 2003), vol. 89, No. 1-2, pp. 1-9.
Office Action (Communication pursuant to Article 94(3) EPC) issued Nov. 21, 2024, by the European Patent Office in corresponding European Patent Application No. 21 943 312.5-1102. (6 pages).

* cited by examiner

*Primary Examiner* — Youngsul Jeong
*Assistant Examiner* — Alyssa L Cepluch
(74) *Attorney, Agent, or Firm* — Buchanan Ingersoll & Rooney PC

(57) ABSTRACT

The present invention provides an industrial method for producing 1,4-dimethylnaphthalene with a small content of 1,3-dimethylnaphthalene. In this method for producing 1,4-dimethylnaphthalene, 5-phenyl-2-hexene is cyclized in the presence of acid catalysts to prepare crude 1,4-dimethyl-1,2,3,4-tetrahydronaphthalene, the crude 1,4-dimethyl-1,2,3,4-tetrahydronaphthalene is dehydrogenized to obtain a crude 1,4-dimethylnaphthalene, and the crude 1,4-dimethylnaphthalene is purified by distillation. In this method, the concentration of 1,3-dimethyl-1,2,3,4-tetrahydronaphthalene in 1,4-dimethyl-1,2,3,4-tetrahydronaphthalene is 1.0% or less with respect to the 1,4-dimethyl-1,2,3,4-tetrahydronaphthalene.

2 Claims, No Drawings

METHOD FOR PRODUCING 1,4-DIMETHYLNAPHTHALENE

CROSS REFERENCE TO RELATED APPLICATIONS

This application is the U.S. National Phase Application of International Application No. PCT/CN2021/111655, titled "METHOD FOR PRODUCING 1,4-DIMETHYLNAPHTHALENE," filed on Aug. 10, 2021, which claims priority to Chinese Patent Application No. 202110633219.5, titled "Method for producing 1,4-dimethylnaphthalene" and filed with the China National Intellectual Property Administration on Jun. 7, 2021, which are incorporated herein by reference in their entirety.

FIELD OF THE INVENTION

The present invention relates to a method for producing 1,4-dimethylnaphthalene (hereinafter, also referred to as "1,4-DMN") containing a small content of isomers, particularly a small content of 1,3-dimethylnaphthalene (hereinafter, also referred to as "1,3-DMN").

BACKGROUND OF THE INVENTION 1,4-DMN is industrially very important as an intermediate raw material of 1,4-naphthalenedicarboxylic acid which is a raw material of resin and dye.

In the above-mentioned field, the isomer content in 1,4-DMN is desirably 1.0% or less, preferably 0.5% or less, and more preferably 0.4% or less.

The production of dimethyl-1,2,3,4-tetrahydronaphthalenes based on the cyclization reaction has been extensively studied mainly on cyclization of 5-O-tolyl-2-pentene (hereinafter also referred to as to synthesize "OTP") 1,5-dimethyl-1,2,3,4-tetrahydronaphthalene (hereinafter also referred to as "1,5-DMT"). 1,5-DMT is important as an intermediate for producing 2,6-naphthalenedicarboxylic acid (hereinafter also referred to as "2,6-NDCA") through a dehydrogenation step, an isomerization step, and an oxidation step.

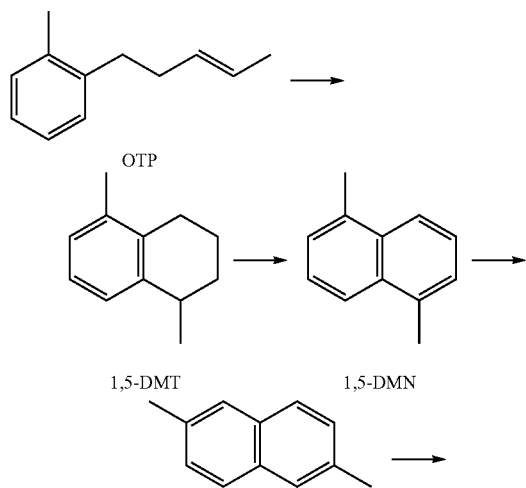

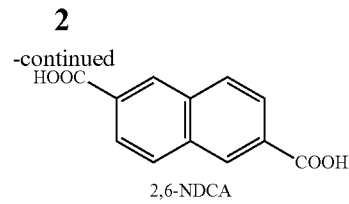

2,6-NDCA

There are many examples of mainly using crystalline silica-alumina catalysts, i.e. zeolite catalysts as OTP cyclization catalysts in liquid-phase and gas-phase reactions (e.g., refer to Patent Documents 1~4).

Since a zeolite catalyst has a strong acidity, a method of cyclizing at 120° C.~250° C. by treatment with alkali metals to adjust the acidity is known (e.g., refer to Patent Document 5). However, the method described in Patent Document 5 has a disadvantage that it is difficult to adjust the acidity.

The cyclization reaction is a violent exothermic reaction, and the dehydrogenation reaction is an endothermic reaction. Techniques for combining cyclization reaction with dehydrogenation reaction have been disclosed. The temperature of dehydrogenation reaction of 1,5-DMT to 1,5-dimethylnaphthalene (hereinafter, also referred to as "1,5-DMN") is higher than the temperature of OTP cyclization reaction. Therefore, a method has been disclosed, in which in order to carry out the cyclization reaction and dehydrogenation reaction in one step, it is necessary to treat the catalysts with alkali metals or the like, and to carry out the cyclization and dehydrogenation in one step at 200° C.~500° C. (e.g., refer to Patent Document 6). In the case of the method described in Patent Document 6, there are problems that the reaction temperature is high, and it is difficult to avoid side reactions such as polymerization, isomerization, etc.

On the other hand, in order to suppress the dimerization of OTP, examples of using diluents or solvents in the cyclization reaction are known (e.g., refer to Patent Document 1, Patent Document 7, and Patent Document 8).

In the production of 1,5-DMN by dehydrogenation reaction of 1,5-DMT, there are many examples in which palladium, platinum, rhenium, etc. are used alone or in the form of supported catalysts in the liquid-phase dehydrogenation reaction. On the other hand, the above-mentioned catalysts, chromia-alumina catalysts, etc. are used in the gas-phase dehydrogenation reaction (e.g., refer to Patent Documents 9 to 12).

As such, many techniques for producing 1,5-DMT or 1,5-DMN from OTP have been studied.

In contrast, production of 1,4-dimethyl-1,2,3,4-tetrahydronaphthalene (hereinafter also referred to as "1,4-DMT") and 1,4-DMN on the basis of cyclization of 5-phenyl-2-hexene (hereinafter also referred to as PH) was also studied.

For example, methods of cyclizing PH using phosphoric acid and/or solid phosphoric acid catalysts are known (e.g., refer to Patent Document 7 and Patent Document 13).

In addition, a method of producing 1,4-DMN via 1,4-DMT from PH in one step by continuously performing gas-phase cyclization and gas-phase dehydrogenation in the presence of hydrogen is also known. (e.g., refer to Patent Document 14). The method of Patent Document 14 describes solid phosphoric acid catalysts as gas-phase cyclization catalysts.

However, as in the case of OTP, the cyclization reaction of PH also uses zeolite as catalysts in the absolute majority (e.g., refer to Patent Document 4, Patent Document 15, Patent Document 16, and Patent Document 17). When 1,4-DMT produced by the method described in the documents is dehydrogenated, there is a problem that the concentration of 1,3-DMN in 1,4-DMN exceeds 1.0%.

For the dehydrogenation of 1,4-DMT, dehydrogenation catalysts known in the documents can be used. Certainly, the method of 1,5-DMT can be applied.

On the other hand, a method of using supported platinum catalysts as gas-phase dehydrogenation catalysts (e.g., refer to Patent Document 14), a method of dehydrogenating 1,4-DMT by controlling specific impurities, etc. are disclosed (e.g., refer to Patent Document 18).

As a purification method of 1,4-DMN, a method of adsorption and separation of 1,3-DMN in a mixture of 1,4-DMN and 2,3-dimethylnaphthalene (hereinafter, also referred to as "2,3-DMN") is known (e.g., refer to Patent Document 19). However, the method of Patent Document 19 has a disadvantage that only a mixture of 1,4-DMN and 2,3-DMN is obtained, and the removal rate of 1,3-DMN is low.

A method of separating 1,4-DMN by removing isomers from a dimethylnaphthalene mixture using adsorbents has been proposed (e.g., refer to Patent Document 20). However, using adsorbents three times or more than dimethylnaphthalene is industrially inefficient.

PRIOR ART DOCUMENT

Patent Document

Patent Document 1: Specification of Korean Patent Application Publication No. 2007-0099241
Patent Document 2: Specification of US Patent Application Publication No. 2007/0232842
Patent Document 3: Japanese Patent H07061941
Patent Document 4: Japanese Patent H03500052
Patent Document 5: Specification of U.S. Pat. No. 5,034,561
Patent Document 6: Japanese Patent H05213782
Patent Document 7: Japanese Patent S49009348
Patent Document 8: Japanese Patent 2000239194
Patent Document 9: Japanese Patent H06072910
Patent Document 10: Japanese Patent S60027694
Patent Document 11: Japanese Patent S48067261
Patent Document 12: Specification of U.S. Pat. No. 3,781,375
Patent Document 13: Japanese Patent S48075557
Patent Document 14: Specification of U.S. Pat. No. 3,775,497
Patent Document 15: Specification of U.S. Pat. No. 5,284,987
Patent Document 16: Specification of U.S. Pat. No. 4,950,825
Patent Document 17: Specification of U.S. Pat. No. 5,401,892
Patent Document 18: Japanese Patent H07069942
Patent Document 19: Japanese Patent 2006199689
Patent Document 20: Japanese Patent S62240632

SUMMARY OF THE INVENTION

The present invention was made on the basis of the above-mentioned circumstances. An object of the present invention is to provide an industrial method for producing 1,4-DMN with a small content of isomers, particularly 1,3-DMN.

The present inventors conducted studies and found that a large amount of 1,3-DMN which is an isomer is contained in 1,4-DMN produced by cyclization and dehydrogenation of PH. However, since the boiling points difference between 1,4-DMN and 1,3-DMN is small, distillation separation of 1,3-DMN from 1,4-DMN is extremely difficult (refer to Table 1 below).

TABLE 1

| | Boiling point (76 0mm Hg) |
|---|---|
| PH | About 210° C. |
| 1,4-DMT | 226° C. |
| | 104~105° C./12 mmHg |
| 1,3-DMT | About 226° C. |
| | 104° C./12 mmHg |
| 1,4-DMN | 265° C. |
| 1,3-DMN | 264.8° C. |
| 5,8-DMT | 254° C. |

It is known that 1,4-DMN is easily isomerized into 1,3-DMN and 2,3-DMN under the action of acid catalysts (e.g., refer to the specification of U.S. Pat. No. 5,118,892). Therefore, isomerization of 1,4-DMN is considered as the cause of the production of 1,3-DMN. However, the present inventors failed to reduce 1,3-DMN in 1,4-DMN in experiments even when 1,4-DMT was dehydrogenated using catalysts without isomerization activity.

The present inventors conducted further studies and found that a considerable amount of 1,3-DMT was present, in addition to a trace amount of 1,3-DMN, in 1,4-DMT produced by the cyclization reaction of PH. 1,3-DMN in 1,4-DMT is in a trace amount (0.01% or less with respect to 1,4-DMT), and cannot be considered as the causative substance of 1,3-DMN in 1,4-DMN. It was found that 1,3-DMT was converted to 1,3-DMN by dehydrogenation, so 1,3-DMN in 1,4-DMN was derived from 1,3-DMT in 1,4-DMT.

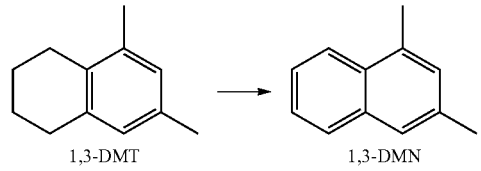

1,3-DMT      1,3-DMN

That is, the present inventors discovered that 1,3-DMT in 1,4-DMT is produced in the cyclization step of PH and is the causative substance of 1,3-DMN in 1,4-DMN, thereby completing the present invention.

One aspect of the present invention is a method for producing 1,4-DMN, comprising cyclizing PH in the presence of acid catalysts to prepare crude 1,4-DMT, dehydrogenating the crude 1,4-DMT to obtain a crude 1,4-DMN, and purifying the crude 1,4-DMN by distillation, wherein the concentration of 1,3-DMT in 1,4-DMT is 1.0% or less with respect to 1,4-DMT.

According to the present invention, an industrial method for producing 1,4-DMN with a small content of isomers, especially a small content of 1,3-DMN, can be provided.

DETAILED DESCRIPTION OF EMBODIMENTS

In the present embodiment, PH can be produced by any methods, and usually obtained via the reaction between ethylbenzene (1) and 1,3-butadiene (2) in the presence of basic catalysts (e.g., alkali metals such as metallic sodium, metallic potassium, etc.). This PH is not pure, and may contain the isomer 5-phenyl-1-hexene, ethylbenzene solvent and the like, and water.

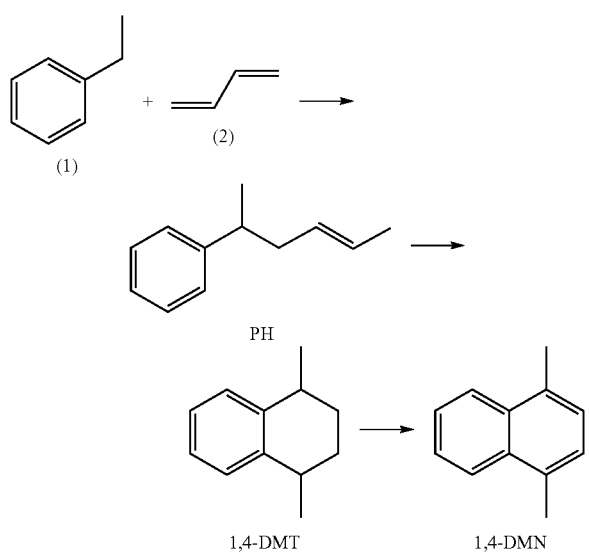

After the basic catalysts are removed from the reaction liquid, PH concentration is increased directly or by distillation, and 1,4-DMT is synthesized by the cyclization of PH under the action of acid catalysts. The cyclization reaction can be carried out intermittently, continuously or semi-continuously in the presence of acid catalysts in the gas or liquid phase. The reaction can be carried out under reduced pressure, normal pressure or increased pressure.

Isomerization catalysts known in the documents can be used as cyclization catalysts. For example, hydrogen chloride, sulfuric acid, phosphoric acid, hydrogen fluoride, sulfonic acids such as p-toluenesulfonic acid, other solid acids such as silica-alumina, etc. can be listed. In the case of a liquid-phase reaction, the catalysts are preferably solid acid catalysts because they are easy to be separated from the cyclization reaction liquid.

As solid acid catalysts, the known isomerization catalysts such as acidic clay, solid phosphate, zeolite (crystalline silica-alumina), amorphous silica-alumina, silica-magnesia, silica-calcia can be used as cyclization catalysts.

The present inventors conducted studies and found that the higher the acidity of the cyclization catalyst is and the higher the reaction temperature under the same catalyst is, the more easily the cyclization reaction proceeds. In addition to 1,4-DMT as the target substance, 1,3-DMT and other by-products are also easily generated.

Most of the zeolite catalysts used in the cyclization reaction are good cyclization catalysts, but they have a disadvantage that the above-mentioned by-products are easily generated due to their high acidity. The zeolite can be treated with alkalis or the like to adjust the acidity, but it is difficult to adjust the acidity. That is, in order to suppress by-products such as 1,3-DMT, it is preferable to carry out a reaction mildly. By-products such as 1,3-DMT can be suppressed via the adjustment of the catalyst amount, reaction temperature, reaction time, etc. by the acidity of catalysts.

The present inventors conducted studies and found that amorphous silica-alumina catalysts are preferable from the viewpoint of keeping the production amount of 1,3-DMT low and maintaining a high reaction rate simultaneously.

As amorphous silica-alumina catalysts, a catalyst whose composition is $SiO_2/Al_2O_3=8\sim2$ in mass ratio is an example. As examples, N631L, N631HN, N632L, N632HN, N633L, N633HN etc. made by Nippon Kasei Co., Ltd. are listed.

As described above, 1,4-DMT, which is a cyclization product of PH, contains a small amount of 1,3-DMN and a considerable amount of 1,3-DMT as impurities, although there is a difference in concentration due to the cyclization conditions.

Among these impurities, 1,3-DMN is in a trace amount, and it is not the main cause of 1,3-DMN in 1,4-DMN. In addition, 1,3-DMN and 1,4-DMT have different boiling points, and can be separated by distillation as needed. However, since there is no difference in boiling points between 1,3-DMT and 1,4-DMT, it is extremely difficult to perform distillation separation (refer to Table 1 above). As described above, since there is no difference in boiling points between 1,4-DMN and 1,3-DMN, it is difficult to perform distillation separation after dehydrogenation reaction. That is, in order to reduce 1,3-DMN in 1,4-DMN, it is preferable to reduce 1,3-DMT in 1,4-DMT.

When amorphous silica-alumina catalysts are used in the liquid-phase cyclization reaction, the addition amount (mass) is preferably 0.02%~10%, more preferably 0.1%~5% with respect to PH, and the reaction temperature is preferably 50° C.~220° C., more preferably 100° C.~200° C., and the reaction time is preferably 1 hour~72 hours, more preferably 2 hours~48 hours. The amount of catalysts can be large, but the cost will increase. When the reaction temperature exceeds 200° C., by-products are likely to be generated.

For example, when p-toluenesulfonic acid is used as a homogeneous catalyst in the liquid-phase reaction, the addition amount (mass) is 0.05%~10%, preferably 0.3%~5% with respect to PH, and the reaction temperature is 100° C.~200° C., preferably 120° C.~180° C., and the reaction time is 0.5 hours~24 hours, preferably 1 hour~12 hours. When the reaction temperature is 200° C. or lower, by-products are less likely to be generated.

In the case of the gas-phase cyclization reaction, the reaction can be performed using solid acid catalysts with low acidity, e.g. amorphous silica-alumina catalysts, in the presence or absence of diluents usually at 220° C.~260° C., preferably 220° C.~250° C. in normal pressure conversion. In order to reduce the concentration of 1,3-DMT with respect to 1,4-DMT, it is better that the acidity of the catalysts is lower, and the reaction temperature is lower, but there is a disadvantage that the reaction is not easy to proceed. In addition, the shorter the residence time in the catalyst layer is, the lower the cyclization rate of PH and the concentration of 1,3-DMT are.

The 1,4-DMT thus obtained can suppress the concentration of 1,3-DMT to 1.0% or less, preferably 0.4% or less with respect to 1,4-DMT. Therefore, even with direct dehydrogenation, the concentration of 1,3-DMN in 1,4-DMN can be made 1.0% or less with respect to 1,4-DMN. The crude 1,4-DMT is preferably purified by distillation. The 1,4-DMT fraction obtained by distillation generated polymers with less catalyst poisons in the cyclization process of PH, and thus has the effect of easily reducing the usage of dehydrogenation catalysts. Certainly, it is also easy to remove 1,3-DMN which exists in a trace amount in 1,4-DMT in a distillation process.

Distillation conditions for 1,4-DMT vary depending on the impurity content. In general, the distillation can be carried out intermittently, continuously or semi-continuously under reduced pressure, normal pressure or increased pressure using a distillation column with theoretical 5~120 stages, preferably 10~80 stages at a reflux ratio of 0.1~30, preferably a reflux ratio of 0.5~10. The higher the number of distillation stages is, or the higher the reflux ratio is, the higher the separation efficiency is, but there are disadvantages of increasing equipment costs and energy consumption.

As dehydrogenation catalysts for 1,4-DMT, the dehydrogenation catalysts known in documents such as nickel-based catalysts represented by Raney nickel catalysts and stabilized nickel catalysts, cobalt-based catalysts, and noble metal catalysts can be used. However, considering from the point of activity, noble metal-supported catalysts, particularly palladium catalysts and platinum catalysts supported on activated carbon are preferable.

As described above, since 1,4-DMN is easily isomerized, it is preferable to select dehydrogenation catalysts that do not cause isomerization of 1,4-DMN produced in the dehydrogenation process.

In the present invention, the dehydrogenation reaction can be carried out in a liquid phase, under reduced pressure, normal pressure, or increased pressure in any of intermittent, continuous, and semi-continuous modes. In addition, in order to perform the dehydrogenation reaction, the reaction can be carried out while inert gas such as nitrogen and argon are blown, or the dehydrogenation reaction can be carried out with the addition of reducing substances such as nitro compounds.

Dehydrogenation can be carried out under boiling of 1,4-DMT, 1,4-DMN, or under boiling of a solvent by adding a solvent.

For example, when dehydrogenation is carried out under normal pressure using a catalyst in which 10% palladium is supported on activated carbon, the addition amount (mass) of the catalyst is preferably 0.05%~10%, more preferably 0.1%~5% with respect to 1,4-DMT, and the reaction temperature is 80° C.~270° C., more preferably 120° C.~270° C., and the reaction time is 0.5 hour~72 hours, more preferably 1 hour~48 hours. The reaction temperature and the reaction time vary greatly depending on the activity of the catalysts, addition of inactive substances or reducing substances, the presence or absence of low-boiling point solvents, etc.

After dehydrogenation, the reaction liquid from which the catalysts were separated contains unreacted 1,4-DMT and 5,8-dimethyl-1,2,3,4-tetrahydronaphthalene (hereinafter, also referred to as "5,8-DMT") which is an isomer of 1,4-DMT, in addition to 1,4-DMN. Distillation purification is performed in order to isolate them. Distillation is generally performed intermittently, continuously or semi-continuously under reduced pressure, normal pressure or increased pressure by using a distillation column with theoretical 10~120 stages, preferably 20~80 stages, at a reflux ratio of 1~60, preferably a reflux ratio of 1~30. The greater the number of distillation stages is, or the greater the reflux ratio is, the better the separation efficiency is, but there are disadvantages of increasing equipment construction costs and energy consumption.

Through distillation and purification, high-purity 1,4-DMN with a small content of impurities can be obtained.

EXAMPLES

Hereinafter, the present invention will be described in more detail by examples, but the present invention is not limited thereto. It should be noted that all compositions (%) are % by mass.

Example 1

(Butadiene Addition)

5.75 kg of ethylbenzene and 25 g of metallic sodium as a catalyst were added into a 10-liter reaction vessel, and 735 g of 1,3-butadiene was added over 10 hours with stirring at 110° C. After the addition was completed, water was added to remove the metallic sodium. This operation was repeated 4 times to obtain 26 kg of the reaction liquid with PH 20.4% and ethylbenzene 55.8%.

19.5 kg of the reaction liquid was distilled in a in a distillation column with theoretical stages of 20 at a reflux ratio of 1~10 to obtain 10.6 kg of a distillate (PH solution) with PH 35% and ethylbenzene 60%.

(Cyclization)

2.8 kg of the above distillate (35% PH solution) and 12 g of amorphous silica-alumina catalysts (SiO2: 83%, Al2O3: 13%) were added into a 5-liter flask equipped with a stirrer and a reflux cooler. With stirring, refluxing was continued while a part of a fraction (solvent) was extracted. The temperature of the reaction liquid was raised to 170° C. over 4 hours, and this temperature was maintained for 6 hours. The catalyst was filtered out from the reaction liquid to obtain 2.06 kg of crude 1,4-DMT having the following composition and unreacted PH of 0.5% or less.

Ethylbenzene: 47%
1,4-DMT: 45%
1,3-DMT: 0.16%

(Dehydrogenation)

1.0 kg of crude 1,4-DMT and 5.8 g of 10% Pd/C were added into a 2-liter flask equipped with a stirrer and a reflux cooler, and ethylbenzene was distilled off from the reflux cooler while the temperature was increased to 250° C. over 4 hours, and this temperature was maintained for 8 hours. The catalyst was filtered out from the reaction liquid to obtain 442 g of crude 1,4-DMN having the following composition.

1,4-DMN: 93.3%
1,4-DMT: 0.9%
5,8-DMT: 2.3%
1,3-DMN: 0.34%

(DMN Distillation)

440 g of the crude 1,4-DMN was distilled in a distillation column with theoretical stages of 40 at 100 mmHg and a reflux ratio of 1~10 to obtain 382 g of purified 1,4-DMN having the following composition.

1,4-DMN: 98.3%
1,4-DMT: 0.4%
5,8-DMT: 0.6%
1,3-DMN: 0.35%

Example 2

(DMT Distillation)

1.0 kg of crude 1,4-DMT of Example 1 was distilled in a distillation column with theoretical stages of 30 at 120 mmHg and a reflux ratio of 5~20 to obtain 426 g of purified 1,4-DMT having the following composition.

1,4-DMT: 98.2%
1,3-DMT: 0.35%

(Dehydrogenation)

400 g of purified 1,4-DMT and 2.4 g of 10% Pd/C were added into a 500-ml flask equipped with a stirrer and a reflux cooler. The mixture was refluxed while the temperature was raised to 250° C. over 4 hours, and this temperature was maintained for 8 hours. The catalyst was filtered out from the reaction liquid to obtain 382 g of crude 1,4-DMN having the following composition.

1,4-DMN: 97.4%
1,4-DMT: 0.9%
5,8-DMT: 1.9%
1,3-DMN: 0.35%

(DMN Distillation)

370 g of the crude 1,4-DMN was distilled by the same method as in Example 1, to obtain 342 g of the purified 1,4-DMN having the following composition.

1,4-DMN: 98.1%
1,4-DMT: 0.4%
5,8-DMT: 0.6%
1,3-DMN: 0.35%

Example 3

(Cyclization)

1.4 kg of the 35% PH solution (distillate) of Example 1 and 6 g of the same amorphous silica-alumina catalyst as in Example 1 were added into a 2-liter flask equipped with a stirrer and a reflux cooler. With stirring, refluxing was continued while a part of a fraction (solvent) was extracted. The temperature of the reaction liquid was raised to 200° C. over 4 hours, and this temperature was maintained for 6 hours.

The catalyst was filtered out from the reaction liquid to obtain 714 g of crude 1,4-DMT with unreacted PH of 0.5% or less.

Ethylbenzene: 17%
1,4-DMT: 63%
1,3-DMT: 0.46%

(DMT Distillation)

700 g of crude 1,4-DMT was distilled in a distillation column having theoretical stages of 30 at 120 mmHg and a reflux ratio of 5~20 to obtain 410 g of purified 1,4-DMT having the following composition.

1,4-DMT: 97.8%
1,3-DMT: 0.71%

(Dehydrogenation)

400 g of purified 1,4-DMT and 3.0 g of 10% Pd/C were added into a 500-ml flask equipped with a stirrer and a reflux cooler. The low-boiling point components were distilled off from the reflux cooler while the temperature was raised to 250° C. over 3 hours. This temperature was maintained for 8 hours. The catalyst was filtered out from the reaction liquid to obtain 380 g of crude 1,4-DMN having the following composition.

1,4-DMN: 96.3%
1,4-DMT: 0.5%
5,8-DMT: 1.3%
1,3-DMN: 0.70%

(DMN Distillation)

370 g of the crude 1,4-DMN was distilled in a distillation column having theoretical stages of 40 at 100 mmHg and a reflux ratio of 1~10 to obtain 322 g of purified 1,4-DMN having the following composition.

1,4-DMN: 97.7%
1,4-DMT: 0.2%
5,8-DMT: 0.4%
1,3-DMN: 0.71%

Example 4

(Cyclization)

1 kg of the 35% pH solution (distillate) of Example 1, 300 g of ethylbenzene and 10 g of p-toluenesulfonic acid were added into a 2-liter flask equipped with a stirrer and a reflux cooler. With stirring, refluxing was continued while a part of a fraction (solvent) was extracted. The temperature of the reaction liquid was raised to 154° C. over 4 hours, and this temperature was maintained for 3 hours.

The catalyst was filtered out from the reaction liquid to obtain 950 g of crude 1,4-DMT having unreacted PH of 0.5% or less.

Ethylbenzene: 57%
1,4-DMT: 32%
1,3-DMT: 0.16%

(DMT Distillation)

700 g of crude 1,4-DMT was distilled in a distillation column having theoretical stages of 30 at 120 mmHg and a reflux ratio of 5~20 to obtain 225 g of purified 1,4-DMT having the following composition.

1,4-DMT: 97.1%
1,3-DMT: 0.49%

(Dehydrogenation)

200 g of purified 1,4-DMT and 1.5 g of 10% Pd/C were added into a 500-ml flask equipped with a stirrer and a reflux cooler. The low-boiling point components were distilled off from the reflux cooler while the temperature was raised to 250° C. over 3 hours. This temperature was maintained for 8 hours. The catalyst was filtered out from the reaction liquid to obtain 190 g of crude 1,4-DMN having the following composition.

1,4-DMN: 96.5%
1,4-DMT: 0.4%
5,8-DMT: 1.2%
1,3-DMN: 0.49%

(DMN Distillation)

180 g of the crude 1,4-DMN was distilled in a distillation column having theoretical stages of 10 at 100 mmHg and a reflux ratio of 1~10 to obtain 171 g of purified 1,4-DMN having the following composition.

1,4-DMN: 97.6%
1,4-DMT: 0.2%
5,8-DMT: 0.9%
1,3-DMN: 0.49%

Comparative Example 1

(Cyclization)

1.4 kg of the 35% PH solution (distillate) of Example 1 and 6 g of the same amorphous silica-alumina catalyst as in Example 1 were added into a 2-liter flask equipped with a stirrer and a reflux cooler. With stirring, refluxing was continued while a part of a fraction (solvent) was extracted. The temperature of the reaction liquid was raised to 210° C. over 2 hours, then the temperature was gradually raised again, and the temperature was raised to 220° C. over 2 hours, and this temperature was maintained for 6 hours.

The catalyst was filtered out from the reaction liquid to obtain 539 g of crude 1,4-DMT having the following composition and unreacted PH of 0.5% or less.

Ethylbenzene: <1%
1,4-DMT: 79%
1,3-DMT: 1.27%

(DMT Distillation)

520 g of crude 1,4-DMT was distilled in a distillation column having theoretical stages of 30 at 120 mmHg and a reflux ratio of 5~20 to obtain 381 g of purified 1,4-DMT having the following composition.
- 1,4-DMT: 96.6%
- 1,3-DMT: 1.55%

(Dehydrogenation)

350 g of purified 1,4-DMT and 3.0 g of 10% Pd/C were added into a 500-ml flask equipped with a stirrer and a reflux cooler. The low-boiling point components were distilled off from the reflux cooler while the temperature was raised to 250° C. over 3 hours. This temperature was maintained for 8 hours. The catalyst was filtered out from the reaction liquid to obtain 324 g of crude 1,4-DMN having the following composition.
- 1,4-DMN: 92.1%
- 1,4-DMT: 0.7%
- 5,8-DMT: 2.3%
- 1,3-DMN: 1.48%

(DMN Distillation)

300 g of the crude 1,4-DMN was distilled in a distillation column having theoretical stages of 40 at 100 mmHg and a reflux ratio of 1~10 to obtain 251 g of purified 1,4-DMN having the following composition.
- 1,4-DMN: 96.5%
- 1,4-DMT: 0.3%
- 5,8-DMT: 0.6%
- 1,3-DMN: 1.55%

Comparative Example 2

(Cyclization)

1.4 kg of the 35% PH solution (distillate) of Example 1 and 6 g of a Y-type zeolite catalyst (Nisui Catalytic Chemicals, H—Y type) were added into a 2-liter flask equipped with a stirrer and a reflux cooler. With stirring, refluxing was continued while a part of a fraction (solvent) was extracted. The temperature of the reaction liquid was raised to 170° C. over 4 hours, and this temperature was maintained for 6 hours.

The catalyst was filtered out from the reaction liquid to obtain 1.03 kg of crude 1,4-DMT having unreacted PH of 0.5% or less.
- Ethylbenzene: 45%
- 1,4-DMT: 43%
- 1,3-DMT: 0.61%

Comparative Example 3

(Cyclization)

1 kg of the 35% PH solution (distillate) of Example 1, 300 g of ethylbenzene and 10 g of p-toluenesulfonic acid were added into a 2-liter flask equipped with a stirrer and a reflux cooler. With stirring, refluxing was continued while a part of a fraction (solvent) was extracted. The temperature of the reaction liquid was raised to 210° C. over 4 hours, and this temperature was maintained for 3 hours.

The catalyst was filtered out from the reaction liquid to obtain 355 g of crude 1,4-DMT having unreacted PH of 0.5% or less.
- Ethylbenzene: 5%
- 1,4-DMT: 77%
- 1,3-DMT: 1.37%

It can be seen from the Examples that the ratio of 1,4-DMN and 1,3-DMN is determined by the ratio of 1,4-DMT and 1,3-DMT in the 1,4-DMN raw materials. 1,3-DMT is produced in the PH cyclization step. The more severe the cyclization conditions are, the easier it is to produce 1,3-DMT.

Therefore, in order to reduce the concentration of 1,3-DMN in the purified 1,4-DMN, it is important to cyclize PH under mild conditions (acidity of the catalyst, catalyst amount, temperature, time, etc.) to reduce the ratio of 1,3-DMT with respect to 1,4-DMT.

The above are only the preferable embodiments of the present invention. It should be noted that for those of ordinary skill in the art, several improvements and modifications can be made without departing from the principles of the present invention. These improvements and modifications should also be regarded as the protection scope of the present invention.

The invention claimed is:

1. A method for producing 1,4-dimethylnaphthalene, comprising: cyclizing 5-phenyl-2-hexene in the presence of an acid catalyst to prepare crude 1,4-dimethyl-1,2,3,4-tetrahydronaphthalene, dehydrogenizing the crude 1,4-dimethyl-1,2,3,4-tetrahydronaphthalene to obtain a crude 1,4-dimethylnaphthalene, and purifying the crude 1,4-dimethylnaphthalene by distillation, wherein in this production method, the acid catalyst is a sulfonic acid or an amorphous silica-alumina catalyst, and the cyclization reaction takes place in a liquid phase at a temperature of 200° C. or lower to make a concentration of 1,3-dimethyl-1,2,3,4-tetrahydronaphthalene in 1,4-dimethyl-1,2,3,4-tetrahydronaphthalene be 1.0% or less with respect to 1,4-dimethyl-1,2,3,4-tetrahydronaphthalene, and wherein a concentration of 1,3-dimethylnaphthalene in 1,4-dimethylnaphthalene is 1.0% or less with respect to 1,4-dimethylnaphthalene.

2. The method for producing 1,4-dimethylnaphthalene according to claim 1, wherein the acid catalyst is an amorphous silica-alumina catalyst.

* * * * *